United States Patent
Bae et al.

[11] Patent Number: 6,055,985
[45] Date of Patent: May 2, 2000

[54] METHODS FOR INJECTING A CONTRAST MEDIUM TO GENERATE PROLONGED UNIFORM VASCULAR ENHANCEMENT

[75] Inventors: Kyongtae T. Bae; Huy Q. Tran, both of St. Louis, Mo.

[73] Assignee: B.H.B., L.C., Chesterfield, Mo.

[21] Appl. No.: 09/289,430

[22] Filed: Apr. 9, 1999

[51] Int. Cl.[7] .................................................. A61B 19/00
[52] U.S. Cl. ........................... 128/828; 604/30; 604/246; 604/187; 600/431
[58] Field of Search .............................. 128/898; 604/30, 604/246, 131, 187; 600/431; 378/8, 95

[56] References Cited

U.S. PATENT DOCUMENTS

| | | | |
|---|---|---|---|
| 4,006,736 | 2/1997 | Kranys et al. | 600/432 |
| 4,210,138 | 7/1980 | Jess et al. | 604/67 |
| 4,213,545 | 7/1980 | Thompson et al. | 222/386.5 |
| 4,695,271 | 9/1987 | Goethel | 604/506 |
| 4,812,724 | 3/1989 | Langer et al. | 318/599 |
| 4,854,324 | 8/1989 | Hirschman et al. | 600/432 |
| 5,269,762 | 12/1993 | Armbruster et al. | 604/155 |
| 5,279,569 | 1/1994 | Neer et al. | 604/154 |
| 5,300,031 | 4/1994 | Neer et al. | 604/154 |
| 5,322,511 | 6/1994 | Armbruster et al. | 604/155 |
| 5,383,858 | 1/1995 | Reilly et al. | 604/152 |
| 5,456,676 | 10/1995 | Nelson et al. | 604/533 |
| 5,583,902 | 12/1996 | Bae et al. | 378/8 |
| 5,662,612 | 9/1997 | Niehoff | 604/155 |
| 5,681,286 | 10/1997 | Niehoff | 604/154 |
| 5,687,208 | 11/1997 | Bae et al. | 378/8 |
| 5,827,219 | 10/1998 | Uber, III et al. | 604/30 |
| 5,840,026 | 11/1998 | Uber, III et al. | 600/431 |
| 5,851,184 | 12/1998 | Goethel et al. | 600/431 |
| 5,865,744 | 2/1999 | Lemelson | 600/407 |
| 5,865,805 | 2/1999 | Ziemba | 604/154 |
| 5,868,710 | 2/1999 | Dane et al. | 604/123 |

*Primary Examiner*—Michael J. Milano
*Assistant Examiner*—Dinh X. Nguyen
*Attorney, Agent, or Firm*—Howell & Haferkamp, L.C.

[57] ABSTRACT

A contrast medium injector for injecting a patient with contrast medium for a CT scan is programmed to provide an injection protocol that is a representation of an ideally defined exponential curve with an initial injection rate decaying at an exponential rate. This has been found to produce a uniform vascular enhancement for the scanning of a patient's blood vessels. The particular exponential decay coefficient which has been found to be optimal is directly proportional to the cardiac output divided by the patient's weight and is approximated at 0.01 for a typical human.

20 Claims, 7 Drawing Sheets

—··— 2exp(-0.007t)mL/s FOR 28 sec.
——— 2exp(-0.017t)mL/s FOR 33 sec.
------ 2exp(-0.026t)mL/s FOR 40 sec.

METHODS FOR INJECTING A CONTRAST MEDIUM TO GENERATE PROLONGED UNIFORM VASCULAR ENHANCEMENT

BACKGROUND OF THE INVENTION

One of the inventors herein is also the inventor of several prior patents related to the improved enhancement of a patient's organ undergoing a computed tomographic scan by controlling the injection of a contrast medium in accordance with a predicted enhancement. These patents include U.S. Pat. Nos. 5,583,902 and 5,687,208, the disclosures of which are incorporated herein by reference. Still other patents have been issued relating to contrast injectors and their use in order to obtain specific enhancement levels. These include U.S. Pat. Nos. 5,827,219; 5,840,026; 5,383,858; 5,662,612; 5,681,286; 5,456,676; and 5,300,031; the disclosures of which are incorporated herein by reference. Still other patents which have been issued and which relate to the field of contrast injectors and their use include U.S. Pat. Nos. 4,006,736; 5,868,710; 4,854,324; 4,210,138; 4,812,724; 5,865,744; 5,279,569; 5,865,805; 4,213,454; 4,695,271; 5,322,511; 5,269,762; and 5,851,184; the disclosures of which are also incorporated herein by reference.

While the use of contrast injectors for injecting a patient with a contrast agent in order to enhance a tissue or organ for CT scanning has been done for years, the first two patents mentioned above, i.e. the '902 and the '208 patents, represent one of if not the earliest attempt to scientifically solve the problem of computing an expected enhancement based upon a patient's physical parameters, assuming a given injection protocol. The inventors work in these prior patents was directed at solving this problem for a patient's organs, using complex differential equations and their solutions to help answer how a human body functions in processing the contrast agent, and then calculating a window of enhancement for which the threshold of desired enhancement is exceeded for a successful scan, assuming a typical injection protocol. As part of the '208 patent, CT angiography was described and its special problems in obtaining high quality scans of blood vessels.

CT angiography (CTA) has been widely accepted, in some cases preferred over conventional angiography, to evaluate the anatomy of major blood vessels such as the aorta and pulmonary artery. In the prior art, the vessels are scanned using a thin-collimation spiral CT technique, while a bolus of contrast medium is injected at a high injection rate (3–5 mL/s) to achieve a high degree of vascular contrast enhancement. Typically, contrast medium is injected at a constant injection rate, i.e. a uniphasic injection protocol is used. This injection scheme results in a steadily rising vascular contrast enhancement profile with a single peak of enhancement occurring shortly after the completion of the injection, as shown by the data collected from a porcine experiment as shown in FIG. 1a. Consequently, vascular enhancement tends to be non-uniform during image acquisition.

Uniform vascular enhancement through the entire period of image acquisition is highly desirable for the purpose of image processing and display, in which 3D postprocessing is frequently based on a threshold CT attenuation value. In addition, it is expected that uniform enhancement would contribute to an optimized usage of contrast medium. In other words, for a given volume of contrast medium, a uniform contrast enhancement whose magnitude is lower than that of a peak enhancement generated by a uniphasic injection would provide a longer temporal window of adequate vascular enhancement than the uniphasic injection presently used in the prior art, thereby resulting in a longer optimal scanning interval. Alternately, it is expected that a smaller volume of contrast medium would be needed to provide a uniform vascular enhancement for the same scanning duration as that achieved by using a uniphasic injection protocol.

In addition to a uniphasic injection protocol, a biphasic injection protocol is sometimes used as well in the prior art. A typical biphasic injection protocol consists of two phases: a short rapid-injection phase, followed by a longer slow-injection phase. A biphasic injection protocol yields more prolonged enhancement than a uniphasic injection protocol, but it generates two enhancement peaks with a valley of enhancement in between. Data collected from another porcine experiment as shown in FIG. 1b supports this conclusion. Each peak occurs shortly after the completion of each injection phase, as might be expected given the results from the first porcine experiment. Although the biphasic might be considered by one less sophisticated as a step in the right direction, it actually increases the complexity of the problem of first of all achieving a level of enhancement which reliably exceeds a threshold and then maintaining an enhancement level above that threshold for a time period that will be adequate to collect the image. As the prior art has little to teach with respect to solving this problem, other than the inventors own work which has not yet focused on the injection protocol aspect of the problem, it would seem that unguided use of a biphasic injection protocol would perhaps increase the amount of contrast agent injected needed to reliably achieve a successful scan over that of a simple uniphasic injection protocol whose enhancement is easier to predict.

The present invention carries the inventor's prior work further by focussing on the injection protocol for CT angiography of the vascular system of a patient, and more particularly by computing an optimum solution of a specific contrast injection protocol for optimizing both the level of enhancement as well as the temporal duration of the enhancement, and an injector to achieve such injection protocol. A byproduct of this invention is as before, the ability to minimize the amount of contrast agent needed to be injected into a patient in order to reliably obtain a successful scan. This is important not only from a cost standpoint as the contrast agent can be expensive, but also from a health standpoint for the patient. The smaller the amount of contrast agent injected into a patient's body the less risk of harmful side effects.

More particularly, the inventors herein have succeeded in developing a contrast injector and a contrast injector protocol for implementation in the contrast injector which optimizes the use of the contrast agent to reliably achieve an enhancement in excess of a preselected threshold and to maintain that "excess" level of enhancement for a temporal duration that is near optimal given the amount of contrast agent used. The contrast injection protocol comprises a ramped, or multiphasic, or exponentially decaying, or steadily decreasing injection rate. An ideal solution is provided by the solution of differential equations describing a simplified compartment model in lieu of the more complex whole body model taught in one of the inventors prior patents mentioned above. This solution renders an exponentially decaying rate of injection having a particular decay coefficient. However, it is contemplated that in the real world, this exponentially decaying injection rate could be approximated by a linearly decay, or ramped decay, or even multi-step decay and yet yield acceptable results in accordance with the teachings of the present invention. Indeed, in the real world, something less than a true exponentially decaying injection rate must necessarily be the physical limit of a contrast injector, even the computer programmable one taught herein as part of the invention. Perhaps even more so as the computer programmable injector uses digital control which in actuality is a series of relatively small steps in changing the injection rate. Still another factor to consider and which also minimizes the precision that might be thought necessary is the varying physiological response between different patients to the injected contrast agent. As such, mathematical precision is not considered as a limit to the present invention.

The particular exponential decay coefficient calculated is proportional to the cardiac output per body weight of the patient. Experimental data with pigs suggests that a decay coefficient of approximately 0.01 would be appropriate for humans. In order to render the injector easier to implement for a typical attending professional, the cardiac output of the patient could be assumed in advance as average and thus no patient specific input need be made in order to achieve an acceptable scan. The experimental data suggested that the decay coefficient designed to generate a uniform enhancement for normal cardiac output resulted in a more dome-shaped enhancement with an increased magnitude for a subject with impaired cardiac output, demonstrating the effect of cardiac output on contrast enhancement. In theory, albeit difficult in the real world, if the degree of cardiac output reduction is known, the exact same uniform vascular enhancement can be reproduced for patients with reduced cardiac output. This can be achieved by lowering the initial injection rate and decay coefficient calculated for patients with normal cardiac output, proportional to the reduction in cardiac output. However, it is apparent that a multiphasic injection protocol designed to achieve a certain level of vascular enhancement in patients with normal cardiac output will not result in overestimation of contrast medium enhancement in patients with reduced cardiac output. The term multiphasic is intended to refer to the injection protocol which is the subject of the present invention. It is to be distinguished from the simple uniphasic or biphasic protocols of the prior art, and represents a protocol which is variable over time in a decreasing fashion whether continuously or discontinuously, ramped, linear, curvilinear, or intermittently.

The duration of aortic enhancement can be prolonged either by increasing the volume of contrast medium for a given initial injection rate or by injecting slowly at a lower initial rate for a given contrast medium volume. With a uniphasic injection, peak magnitude of aortic enhancement depends on three injection factors, i.e. the concentration, injection rate, and total volume of contrast medium. With a multiphasic injection protocol, however, the peak magnitude can be independent of the total volume of contrast medium, provided that the volume is not too small to reach an initial upslope enhancement to a plateau or threshold level. Thus, multiphasic injection is advantageous over uniphasic injection when a prolonged duration is desired, while keeping contrast enhancement from rising, by increasing the volume of contrast medium. Using the teachings of the present invention, this multiphasic injection protocol represents the ideal protocol to reliably achieve a uniform enhancement in excess of a threshold value for a desired temporal window as necessary for a vascular scan.

While the principal advantages and features of the present invention have been briefly explained, a fuller understanding of the invention may be gained by referring to the drawings and the detailed description of the preferred embodiment which follows.

DETAILED DESCRIPTION OF THE PREFERRED EMBODIMENT

Now will be explained the methodology for calculating the multiphasic solution for achieving a uniform vascular enhancement.

The distribution of contrast medium in a blood vessel depends on the circulating blood flow and blood volume of the vessel. Although a whole body model provides a complete description of enhancement characteristic in each vessel and each organ, modeling with a limited number of compartments is less complex and more approachable for theoretical analysis of various injection parameters. There are various ways to model body compartments. An optimal model is the one that uses the smallest number of compartments, but adequately describes the underlying pharmacokinetic process. An approach frequently used in prior art studies of drug distribution is to model the whole body with two compartments, whereby contrast medium is introduced into a central plasma compartment, distributed to a peripheral extracellular compartment, and then eliminated from the central plasma compartment by renal excretion. Although this scheme is sufficient for describing the late pharmacokinetics of contrast medium (hours), it needs further refinement to be applied to the description of early pharmacokinetics (minutes).

Figure 2:
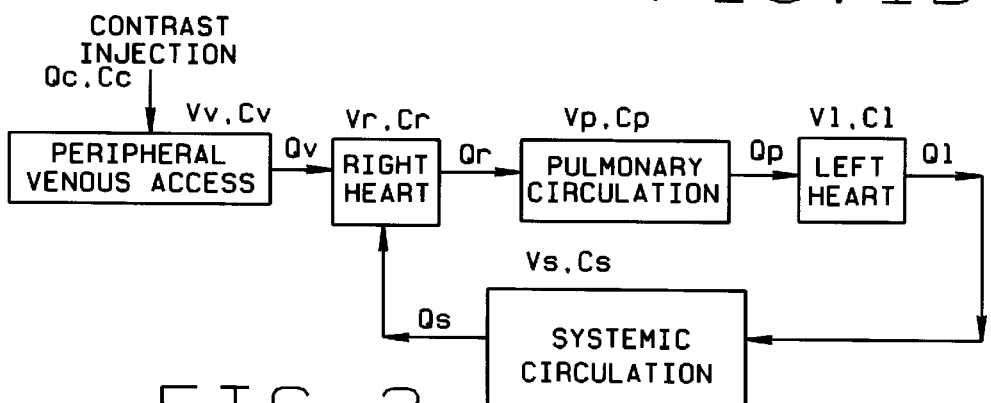
FIG. 2 is a block diagram depicting a compartment model for early pharmacokinetics of contrast enhancement.

FIG. 2 shows a compartment model which is designed to simulate early contrast enhancement in the aorta. In this model, contrast medium is injected into the antecubital vein and distributed to the right heart, the pulmonary compartment, the left heart, and the aorta. It then recirculates back to the right heart via the systemic circulation. This transport scheme is specifically simplified to focus on early pharmacokinetics of the aortic contrast enhancement, thus reducing the complexity of our analysis. For example, a constant elimination of contrast medium from the central blood compartment by renal excretion (transport to urine) is only substantial in late pharmacokinetics and thus not considered in this simple compartment model.

The model in FIG. 2 is described mathematically as follows. Let Cv, Cr, Cp, Cl, and Cs be the contrast concentrations in the peripheral vein (from the antecubital to the right heart, right heart, pulmonary, left heart, and systemic circulation, respectively. Vv, Vr, Vp, Vl and Vs represent the corresponding compartment (blood and interstitial) volumes of the peripheral vein, right heart, pulmonary, left heart, and systemic circulation, respectively. Qv is the volumetric flow rate of blood leaving the peripheral vein. Qr, Qp, Ql, and Qs are equivalent and represent the cardiac output of the system. Cc and Qc are the concentration and volumetric flow rate of injected contrast medium, respectively. During contrast injection, all the volumetric blood flow rates (Qv, Qr, Qp, Ql, and Qs) are increased by Qc. The governing equations for the model are written from mass balance equations for each compartment (Equations 1–5 in Appendix A).

The aortic enhancement curves were computer simulated by numerically solving Equations 1–6 in Appendix A. The physiological parameters used in the model for humans include 40 mL for Vv (peripheral vein), 250 mL each for Vr (right heart) and for Vl (left heart), 600 mL for Vp (pulmonary circulation), and 10 L for Vs (systemic circulation). Associated volumetric blood flow rates are 250 mL/min or 4.2 mL/sec for Qv and 6.5 L/min for the cardiac output. These values were estimated based on published human physiology data for a standard adult. To mimic channels of blood vessels, the peripheral venous compartment and pulmonary compartment are further divided into multiple smaller compartments in series (5 subcompartments for the peripheral venous compartment and 30 subcompartments for the pulmonary compartment).

Since detailed cardiovascular physiologic data for porcine models are rather lacking compared to human models, the inventors rescaled the above human physiological parameters to determine the physiological parameters for the porcine model. The compartment volumes of the porcine model were estimated by multiplying the compartment volumes of a standard 70 kg human model by the body weight ratio, e.g. for a 25 kg pig, the ratio is 25:70. It is known that the average cardiac output per body weight of pigs is twice as high as that of humans. Therefore, the cardiac output for a 25 kg pig corresponds to that of a 50 kg human. Although there is some subjectivity in selecting these parameters, they were estimated within available physiologic data and represent simply a set of reference values for simulation to compare with experimental data.

A total of 38 ordinary differential equations were used to describe the model in FIG. 2. These equations were solved using numerical integration programs of fifth-order Runge-Kutta method. This model was run at a personal computer and took less than a fraction of a second to compute. The contrast concentration curve over time was calculated for each region by solving these differential equations for a given contrast injection protocol. After the contrast concentration in each compartment was computed by solving Equations 1–6, it was translated into a CT enhancement value.

For a given input injection protocol, the mathematical model described above can be used to predict the output contrast enhancement curve of the aorta. Conversely, the model can be used to solve the inverse problem, i.e. to predict an input function for a given output contrast enhancement profile. Solving for an input contrast injection algorithm which will generate a prolonged, uniform vascular contrast enhancement is the focus of the present invention.

The inverse problem can be solved directly by the Laplace Transform of governing equations in the model with a given desired constant aortic enhancement and initial conditions. Mathematical manipulation for the solution is detailed in Appendix A. This solution, i.e. a contrast injection profile, was in turn applied as an input to the mathematical model to simulate and verify the reproducibility of desired constant aortic contrast enhancement. Simulation was performed for both porcine and human mathematical models by adjusting the physiological inout values. Different injection profiles were tested to study how they affect aortic contrast enhancement. In addition, the effect of reduced cardiac output on the enhancement was investigated. The model was modified by decreasing the cardiac output by 20% and 40%. Contrast enhancements were simulated in this model with the input injection which, when used in normal cardiac output, would produce a uniform contrast enhancement. The patterns of these enhancements were compared with that from normal cardiac output.

In order to test the mathematical solutions, a porcine study was conducted. All animal care and procedures performed were approved by the Institutional Animal Study Committee. Four pigs weighing initially 24–26 kg underwent scanning in two or three separate sessions. Each session was separated by at least two days. Two pigs had all their sessions within a week, while the other two pigs had their first two and last sessions delays 4–5 weeks, which results in an increase in their weight to 35–40 kg in their last session.

In each session, the pig was anesthetized, intubated, and underwent scanning for three or four sets of images obtained in random order. During scanning, each pig was ventilated with oxygen and low tidal volume to minimize breathing motion artifact. Each image set consisted of 27 dynamic CT sections (5 mm collimation) acquired at a fixed mid-abdominal aortic level, following i.v. injection of contrast medium into a peripheral vein. Each set of scans were 45–60 minutes apart to minimize the effect of prior contrast administration. All CT scanning was performed with a Somatom Plus-S scanner (Siemens Medical Systems, Iselin, N.J.) using a one-second scanning time and a one-second interscan delay.

Figure 3:
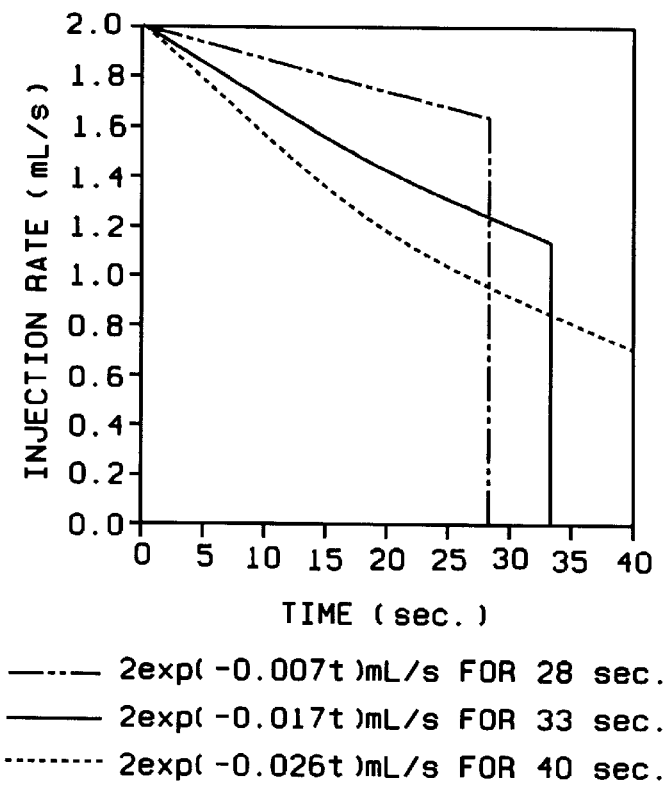
FIG. 3 is a graph of three multiphasic injection profiles with the initial injection rate of 2 mL/s and different exponential decay constants.

Three types of injection schemes were tested: uniphasic, biphasic, and multiphasic. Biphasic injections were performed by a prior art power injector which was used in routine clinical CT scanning while uniphasic and multiphasic injections were conducted with a power injector which was invented for achieving the required protocols. This power injector was capable of delivering contrast medium in various uniphasic or multiphasic injection algorithms, as is explained in greater detail below. The multiphasic injection rate is determined by an initial injection rate and an exponential decay coefficient, as shown in FIG. 3. The total injected volume of contrast medium corresponds to the integrated sum of the multiphasic injection over injection duration.

Most injections were performed with the initial injection rate of 2 mL/s. Volumes of contrast medium used were 50, 70 and 90 mL of iothalmate meglumine (Conray 60; Mallinckrodt Medical, St. Louis, Mo.; 282 mgI/mL). Three differential exponential decay coefficients (0.007, 0.017, 0.026) were tested. These coefficients were initially designed as (0.01, 0.02, 0.03), respectively, until further testing and verification revealed discrepancies between the design and actual values. These were the three smallest discrete increments allowed in the prototype of the inventive power injector. Decay coefficient higher than 0.03 was not used because it was evident that a further increase in the coefficient would deviate further away from uniform vascular enhancements. A uniphasic injection was determined as being equivalent to a zero exponential decay coefficient where the injection rate remains constant at an initial injection rate throughout the injection duration.

Most extensively tested and compared injections were 50 mL total of contrast medium injected by a uniphasic injection of 2 mL/s and by a multiphasic injection of 2 mL/s initial rate having an exponential decay coefficient of 0.017. The same injection methods were repeated but with an increased total contrast medium volume to 70 mL or with both increased injection rate to 3 mL/s and increased volume to 90 mL. Other injections studied include biphasic injections of 50 mL (2 mL/s for 12 sec and then 1.4 mL/s for 18 sec) and 70 mL of contrast medium mL (2 mL/s for 17 sec and then 1.0 mL/s for 36 sec). Approximately half of the total contrast volume was injected in each phase of the biphasic injections. The first and second injection rate of the biphasic injections were determined by the initial and final injection rates of the multiphasic injections with an exponential decay coefficient 0.017 of a corresponding total contrast medium volume, respectively.

Attenuation values of the aorta were measured from post-contrast scans (at the same level as the pre-contrast scans) using a circular region of interest (ROI) at the center of the aorta. Contrast enhancement was calculated as the absolute different in attenuation value between the pre- and post-contrast scans. For the data analysis, the injection duration (ID), the magnitude of peak aortic enhancement (PA), and the uniformity of enhancement :the duration of the enhancement achieved with 90% of the peak: 90%DCF. were evaluated. Means and standard deviations were also computed. The results are now explained.

Figure 1A:
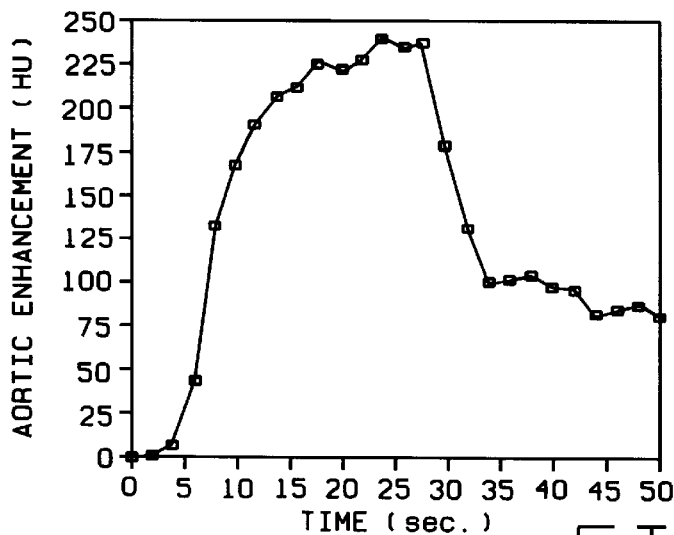
FIGS. 1a and 1b are graphs of empiric time-enhancement curves from a 25 kg pig using (a) uniphasic and (b) biphasic injections.
Figure 1B:
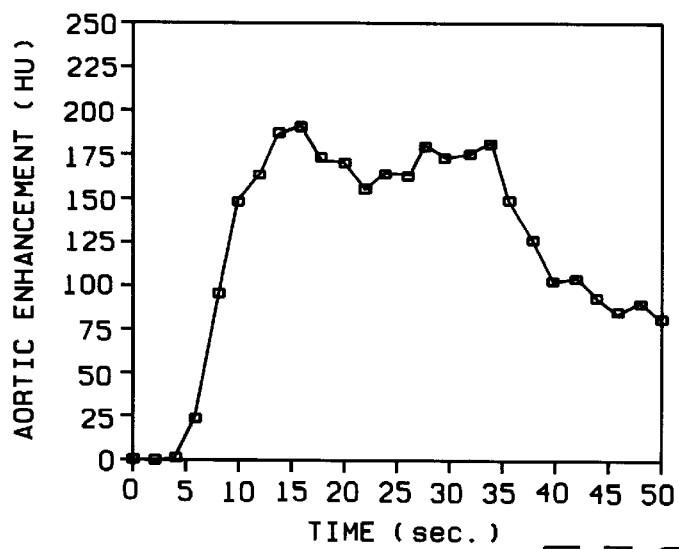
Figure 4:
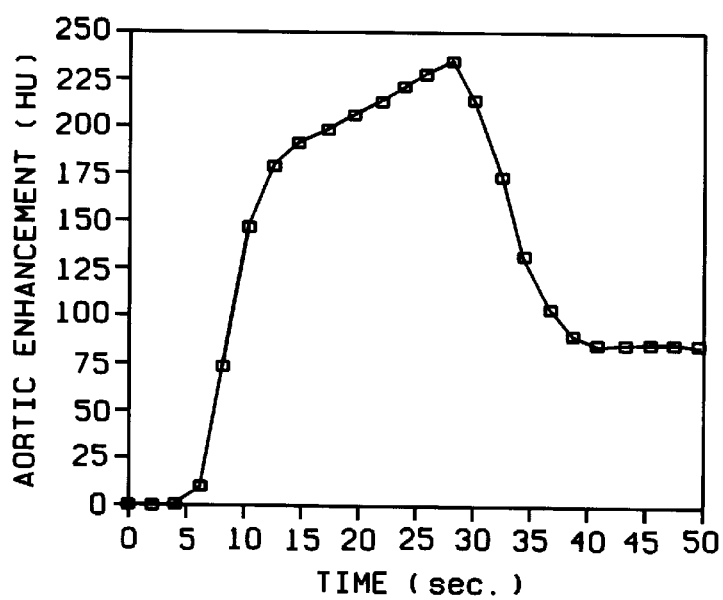
FIG. 4 is a graph of a simulated porcine aortic enhancement curve.

FIG. 4 shows a simulated aortic enhancement curve generated from the model for a 25 kg pig with 50 mL of 282 mgI/mL contrast medium injected at a uniphasic 2 mL/sec. This curve was in good agreement with an empiric aortic enhancement curve observed in a 25 kg pig (FIG. 1A), including the time to and the magnitude of the peak aortic enhancement (simulated vs. empiric: 28 vs. 26 sec and 234 vs. 250 HU). These curves differed notably at the after-peak portion when the recirculation of contrast becomes substantial with the discontinuity of contrast injection. This portion was simplified in the model which mainly focused on the early part of the injection protocol, i.e. the first pass of contrast bolus pharmacokinetics.

The contrast injection algorithm that provided a uniform, prolonged vascular enhancement was solved as shown in Appendix A. The solution, i.e. contrast injection protocol is expressed as the product of an initial rejection rate and an exponential function of time, as shown in Equation 15. The exponential decay coefficient equals Q/Vs, the ratio of the cardiac output to the systematic volume of distribution of contrast medium, which is itself proportional to the cardiac output per body weight.

Figure 5A:
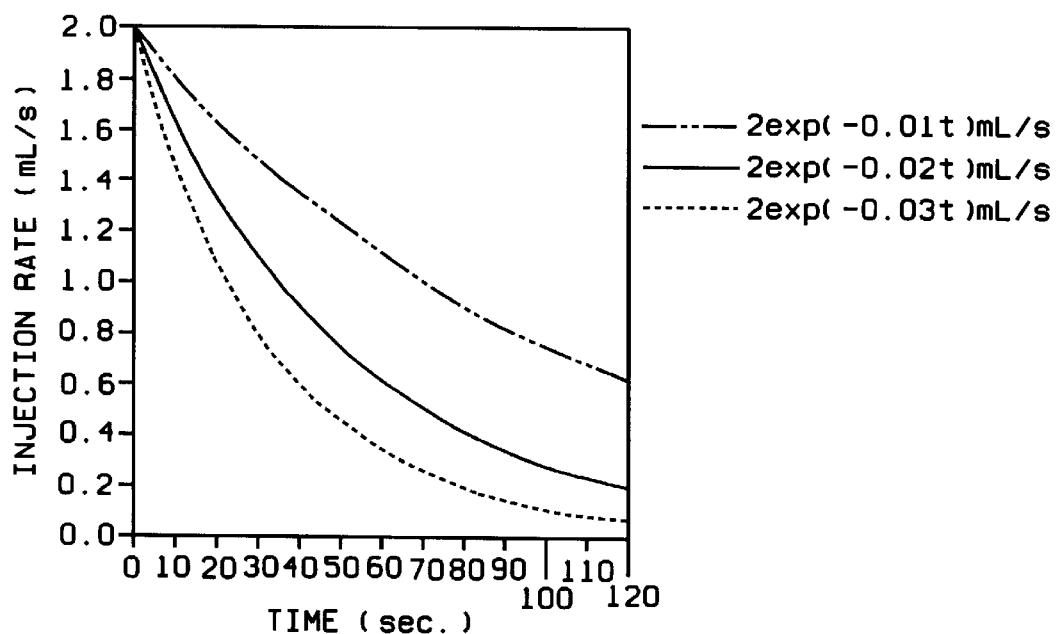
FIGS. 5a and 5b are graphs of three exponential injections and their corresponding simulated porcine aortic contrast enhancements.
Figure 5B:
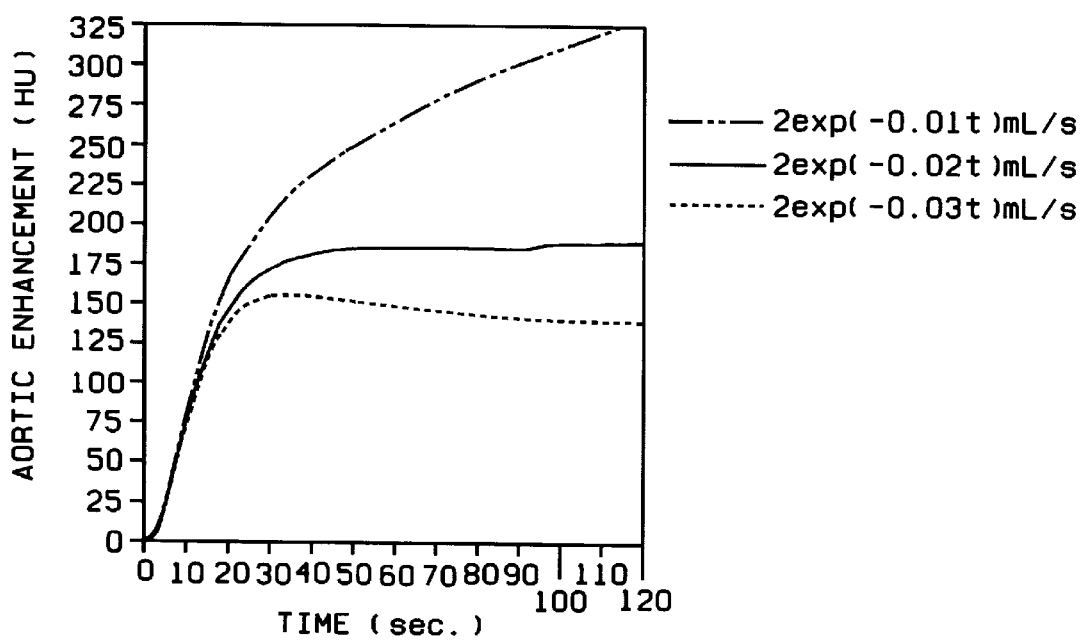

FIG. 5a shows three exponential injection profiles with a 2 mL/s initial injection rate and decay coefficients (0.01, 0.02, and 0.03) for a 120 sec injection duration. The total amount of contrast medium in each injection is represented by the area under each curve. A lower exponential decay resulted in a higher total amount of contrast medium and a higher final injection rate at 120 sec. Aortic contrast enhancement curves corresponding to these exponential injection profiles were simulated from the mathematical model (with porcine physiological parameters) by solving Equations 1–6 and are depicted in FIG. 5b. Uniform, plateau aortic enhancement was observed with an exponential decay constant of 0.02 (Q/Vs=77/3571=0.021). With decay coefficients 0.01 or 0.03, contrast enhancement either steadily rises above this plateau level or declines after a peak below the plateau level, respectively.

Figure 6:
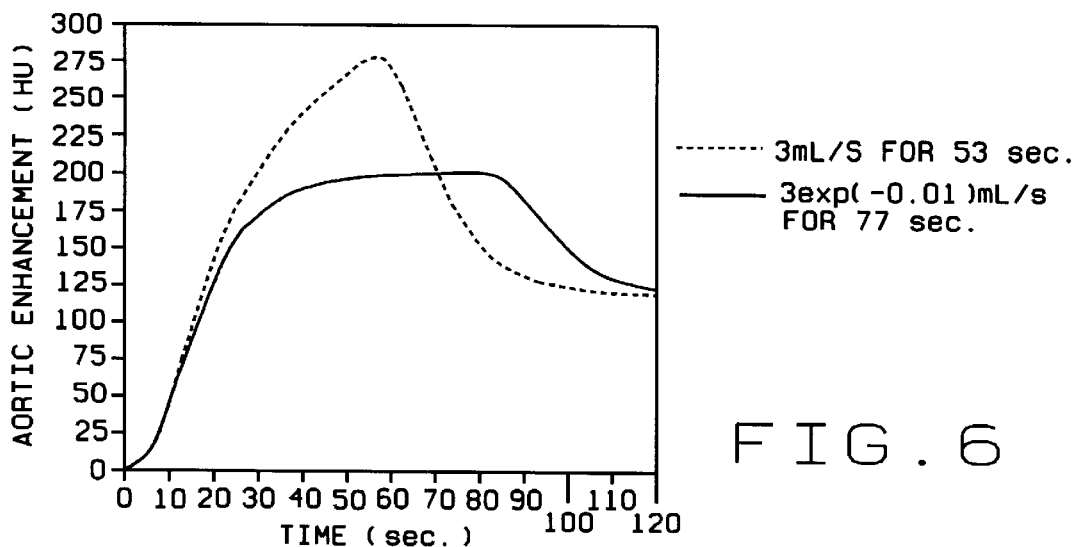
FIG. 6 is a graph of a simulated aortic contrast enhancement curve in a human model with uniphasic and multiphasic exponential injections.

FIG. 6 shows two simulated aortic enhancement curves for a human model using uniphasic or multiphasic injection protocols with 0.01 (Q/Vs=108/10000) exponential decay injections at an initial injection rate of 3 mL/s for a total of 160 mL of contrast medium. A prolonged, uniform contrast enhancement was achieved with the multiphasic injection protocol. Notice that this exponential decay coefficient for the human model is approximately half that of the porcine model, reflecting the physiological values used in the model that the average cardiac output per body weight for humans is half that for pigs.

Figure 7:
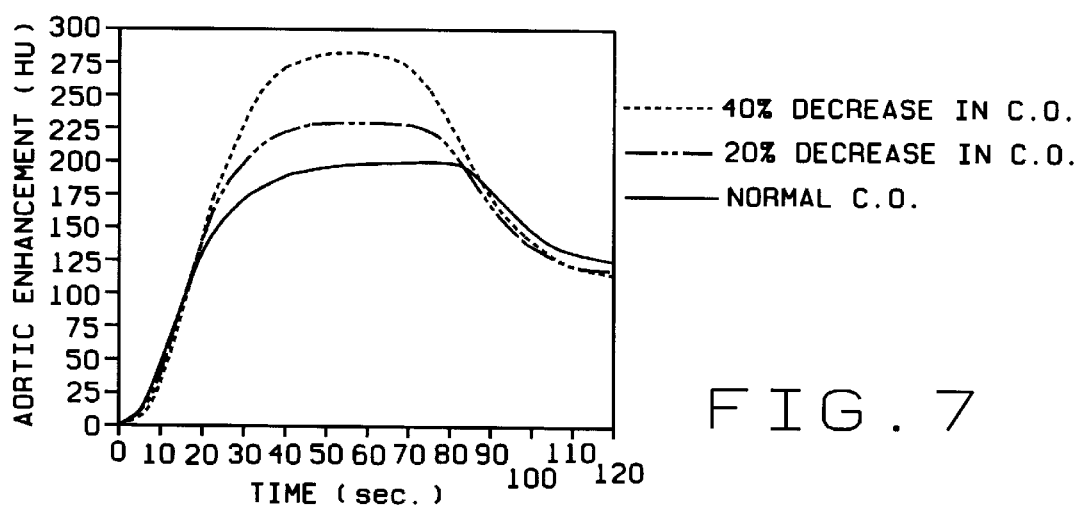
FIG. 7 is a series of simulated aortic contrast enhancement curves in a human model with normal and reduced cardiac outputs.

The effect of reduced cardiac output on the enhancement was evaluated by reducing the cardiac output by 20 and 40% in the model. The exponential injection with a decay coefficient 0.01, which generates a uniform enhancement for normal cardiac output CQ=108 mL/s), was used as the input contrast injection to this model with reduced cardiac output. The output simulated aortic enhancements are shown in FIG. 7. As shown therein, the contrast enhancement curves become more dome-shaped with an increase in magnitude, as the cardiac output decreases.

Figure 8A:
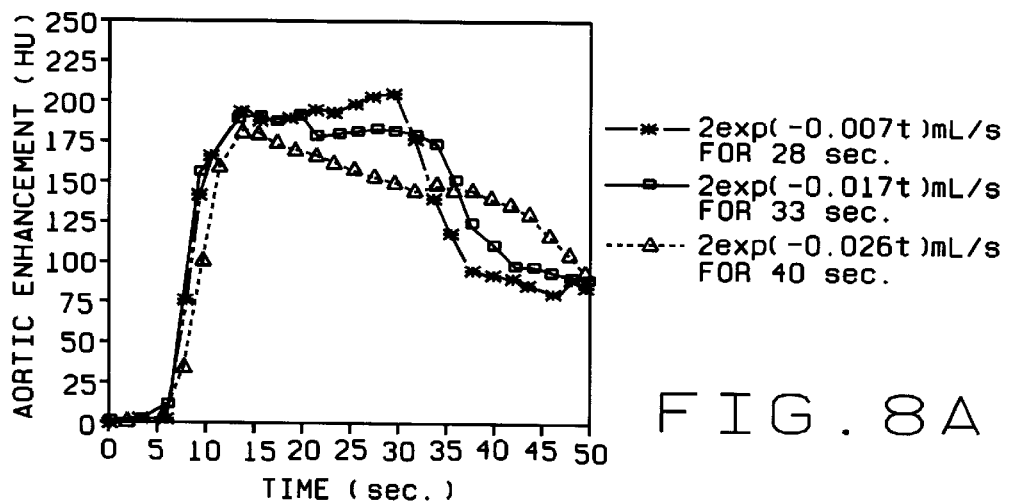
FIGS. 8a and 8b are empiric porcine aortic enhancement curves using multiphasic exponential injections in a 25 kg pig and a 40 kg pig.
Figure 8B:
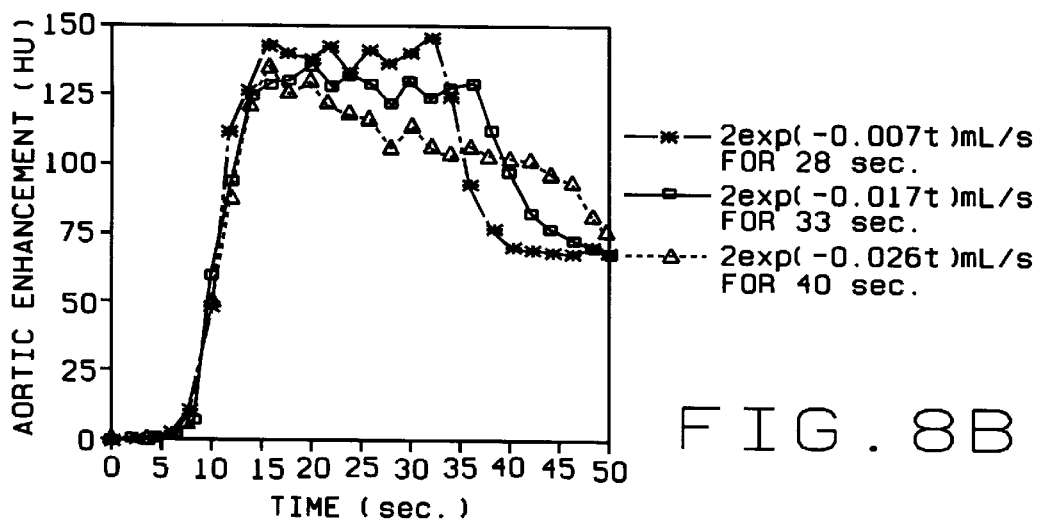

FIG. 8 demonstrates the empiric porcine aortic enhancement curves obtained for two pigs using multiphasic exponential injections with three different exponential decay coefficients (0.007, 0.017, 0.026). The contrast injection profiles are described in FIG. 3. Exponential injection with a decay constant of 0.017 showed the aortic enhancement to be more uniform than with other injection protocols. This result was compatible with the theoretical model prediction that an exponential injection with a decay constant of 0.02 provided a plateaued aortic enhancement. Injections with lower (0.007) or higher (0.026) decay constant resulted in aortic enhancements steadily rising or declining after a peak, respectively, as predicted by the theoretical model. The magnitude of aortic enhancement in FIG. 8a was substantially higher than that in FIG. 8b, reflecting the difference in body weight between two pigs t25 kg vs. 40 kg). However, the patterns of aortic enhancement produced by three different exponential decay coefficients were consistent.

Figure 9A:
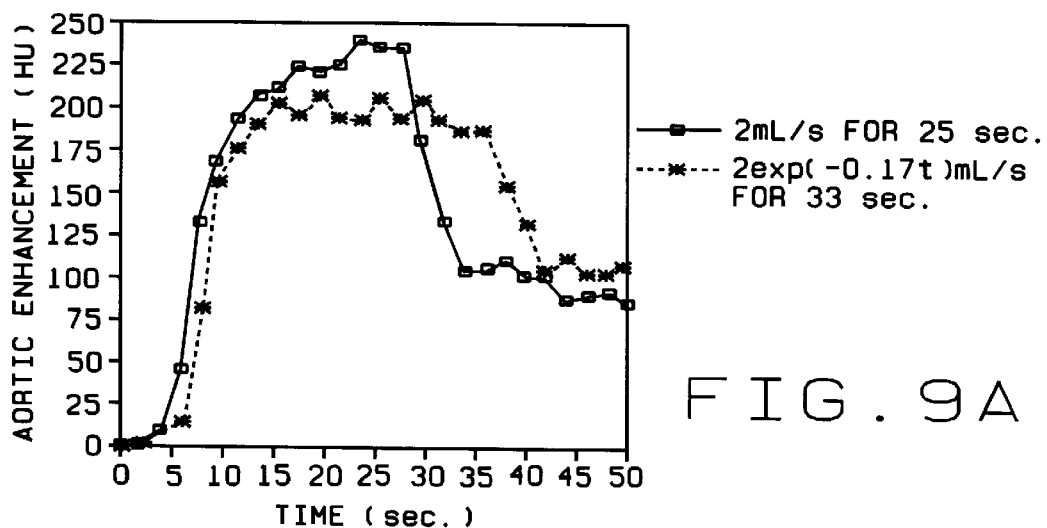
FIGS. 9a and 9b are graphs of the empiric porcine aortic enhancement with uniphasic and multiphasic injections of 50 mL and 70 mL contrast medium.
Figure 9B:
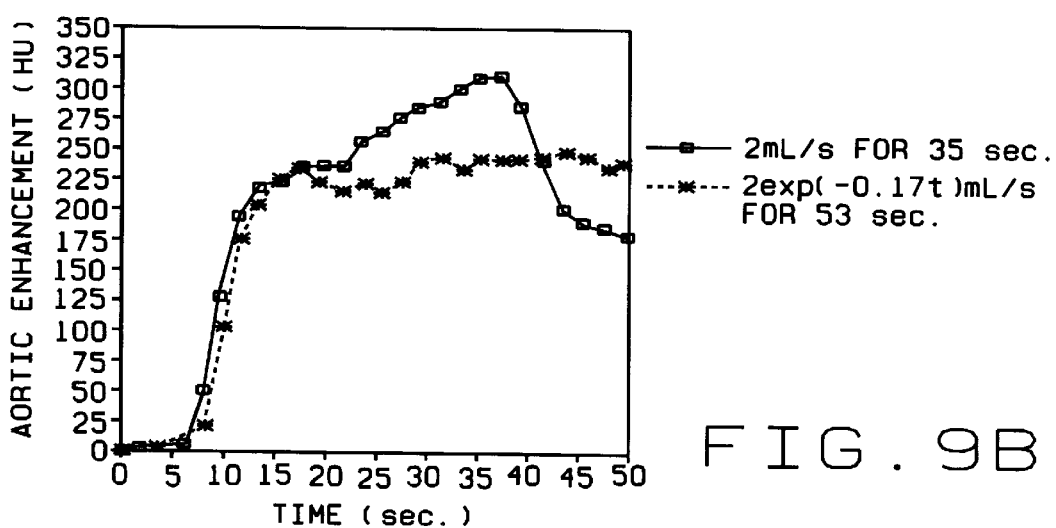

Aortic enhancement curves in two pigs experiencing unichasic and multiphasic exponential injections are shown in FIG. 9 for (a) 50 mL and (b) 70 mL of contrast medium. The unichasic injection used a contrast injection rate of 2 mL/s, while the multiphasic injection started at 2 mL/s but declined exponentially with a decay constant 0.017. The illustrated results clearly demonstrate that multiphasic injections yielded more prolonged and uniform vascular enhancement than uniphasic injections. Performance of the multiphasic compared with the uniphasic injection can be summarized for four pigs as follows. For a 2 mL/s initial injection rate of 50 mL contrast medium, the multiphasic injection increased ID by 30%, reduced PA by a mean of 19%, and increased 90% DCE by a mean of 81%. For 70 mL injections with a 2 mL/s initial injection rate, ID increased by 51%, PA decreased by 18%, and 90% DCE increased by 94%.

Figure 10A:
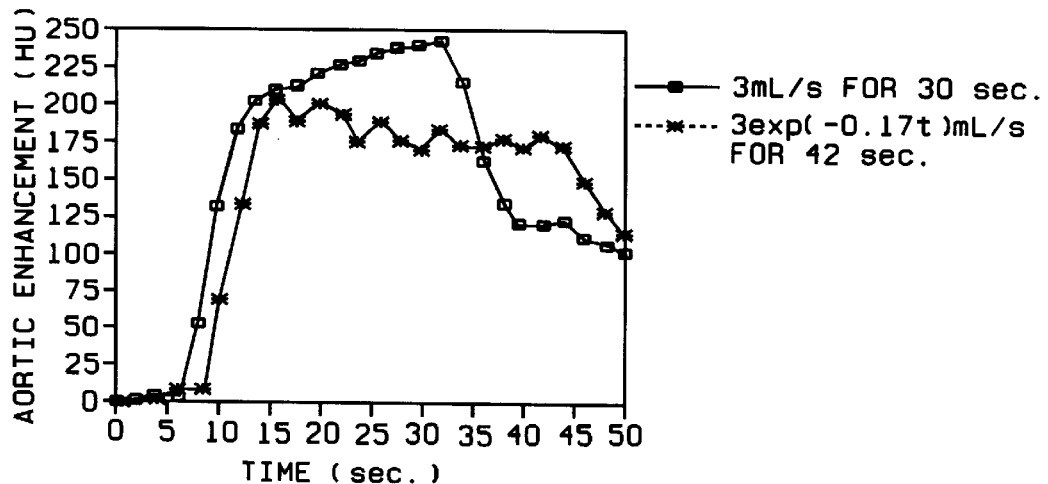
FIGS. 10a and 10b are graphs of empiric porcine aortic enhancement curves generated by various injections with 90 mL and 70 mL contrast medium.
Figure 10B:
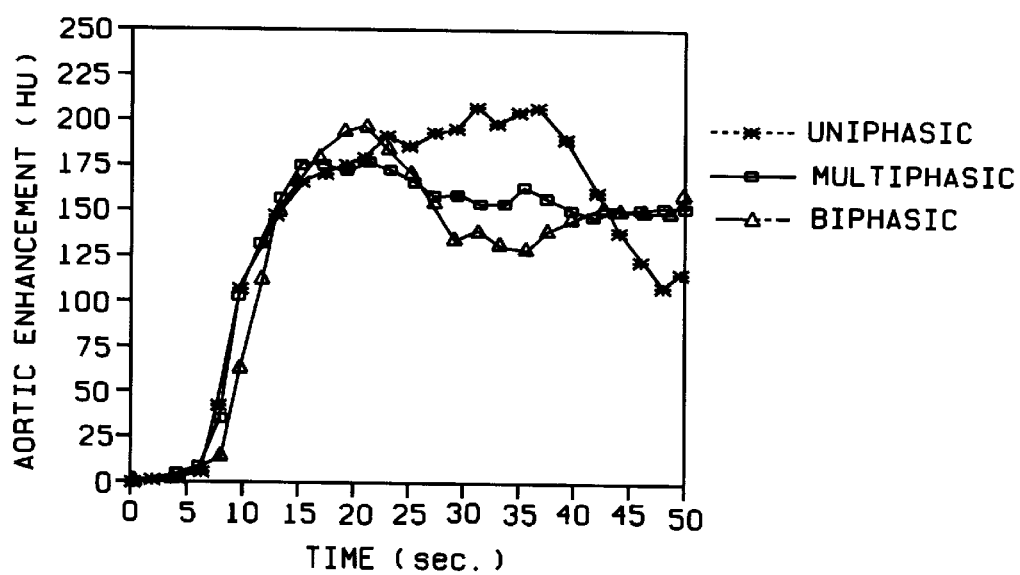

FIG. 10a shows empiric aortic enhancement curves in a 40 kg pig obtained with uniphasic and multiphasic exponential (decay coefficient 0.017) injections with a 3 mL/s initial injection rate and 90 mL of contrast medium. In this pig, the multiphasic injection method resulted in more prolonged, uniform but slightly declining aortic enhancement. FIG. 10b demonstrates three empiric aortic enhancement curves generated by uniphasic, multiphasic and biphasic injections of 70 mL of contrast medium. The uniphasic injection consisted of a 2 mL/s injection for 35 sec, while the multiphasic injection had an initial rate of 2 mL/s with a decay coefficient of 0.017 for 53 sec. The biphasic injection was performed with a 2 mL/s rate for 17 sec and then a 1.0 mL/s rate for 36 sec. Multiphasic injections again yielded more prolonged and uniform vascular enhancement than uniphasic injections. A biphasic injection resulted in more prolonged enhancement than a unichasic injection but generated two enhancement peaks with a valley in between.

A prolonged, uniform vascular enhancement is desirable in CT angiography and some chest CT applications where the vessels, not the parenchyma of organs, are the target of interest. This enhancement pattern is useful for the purpose of image processing and display, in which 3D postprocessing is frequently based on a threshold CT attenuation value. It may also provide a longer optimal scanning interval for a given volume of contrast medium than a single-peaked contrast enhancement generated by a conventional uniphasic injection. Alternatively, it may enable the use of a lower volume of contrast material for a given scanning duration.

Prolonged, uniform aortic contrast enhancements can be achieved by multiphasic exponential injections with adequately selected decay coefficients in accordance with the teaching of the present invention. The multiphasic injection protocol was mathematically derived from a physiologically-based pharmacokinetic model, and then a porcine model was used to confirm findings observed in theoretical analyses and computer simulations. Although further clinical studies are warranted to validate the findings and injector performance, it is expected from previous experiences in comparative studies and pharmacokinetics that a human model would behave similarly.

A simplified compartment model which has a limited number of compartments, instead of a more complex whole body model was used. The current compartment model was designed specifically to solve for a contrast injection profile which generates a prolonged, uniform vascular enhancement. This simple model does not provide a complete description of enhancement characteristics in each organ but can adequately describe the underlying pharmacokinetic process of interest, i.e. first-pass enhancement characteristics of the aorta. In this respect, the simulated results correlated well with the experimental results from the porcine model. Since the model equations 1–5 in Appendix A do not include renal or other clearance from the systemic circulation, the contrast concentration maintains a steady plateau following the cessation of contrast injection. This may not be a significant factor in scans of less than 5–1min duration.

The fact that a multiphasic exponential injection generates a uniform vascular enhancement can be explained conceptually as follows. Contrast enhancement in a system is proportional to the net amount of contrast medium present, i.e. inflow minus outflow contrast medium. Aortic enhancement reflects an accumulation of contrast medium in the central blood volume (i.e. contrast medium injected and recirculated minus medium diffused away from the vessel). Thus, vascular enhancement rises when the rate of contrast material infusion into the central blood volume exceeds the rate at which contrast medium diffuses away. This physiological event explains that aortic enhancement peaks shortly after the completion of the injection with a uniphasic injection, representing the maximal accumulation of contrast medium within the central blood volume compartment. The rate at which contrast medium leaves the central blood compartment to the interstitium compartment is likely proportional to the concentration gradient between the two compartments, i.e. an exponential function of time, because the contrast transport phenomenon is governed by passive diffusion and permeability. Thus, when the outflow rate of contrast medium is balanced by the infusion rate of contrast medium by a multiphasic exponential injection protocol, a uniform vascular enhancement occurs.

The experimental results showed that proper selection of a decay coefficient in multiphasic exponential injections was crucial to generate uniform vascular enhancement. The decay coefficient was proportional to the cardiac output per body weight. Since the cardiac output per body weight in humans is half that of pigs, a 0.01 decay coefficient would be adequate for humans. This value, which is already normalized by body weight, is independent of body weight. For example, a multiphasic injection with a 0.017 decay coefficient resulted in a similar uniform vascular enhancement pattern but with a decrease in magnitude in the same pig scanned at its baseline weight of 25 kg and later after gaining 15–20 kg.

The decay coefficient designed to generate a uniform enhancement for normal cardiac output resulted in more dome-shaped enhancement with increased magnitude when there is a reduced cardiac output, demonstrating the effect of cardiac output on contrast enhancement. In theory, albeit difficult in practice, if the degree of cardiac output reduction is known, the exact same uniform vascular enhancement can be reproduced for patients with reduced cardiac output. This can be achieved by lowering the initial injection rate and decay coefficient calculated for patients with normal cardiac output in an amount proportional to the reduction in cardiac output. However, it is apparent that a multiphasic injection designed to achieve a certain level of vascular enhancement in patients with normal cardiac output will not result in overestimation of contrast medium enhancement in patients with reduced cardiac output.

The duration of aortic enhancement can be prolonged either by increasing the volume of contrast medium for a given initial rejection rate or by injecting slowly at a lower initial rate for a given contrast medium volume. With a uniphasic injection, peak magnitude of aortic enhancement depends on three injection factors, i.e. the concentration, injection rate, and total volume of contrast medium. With a multiphasic injection, however, the peak magnitude can be independent of the total volume of contrast medium, provided that the volume is not too small to reach an initial upslope enhancement to a plateau level. Thus, a multiphasic injection protocol is advantageous over a uniphasic injection when a prolonged duration is desired, while keeping contrast enhancement from rising, by increasing the volume of contrast medium.

Although the theoretical analysis indicated that a multiphasic injection should follow an exponential decay to generate a prolonged, uniform vascular enhancement, other functional patterns may be used to approximate an exponential decay. For example, a short segment of an exponential curve can be approximated by a linear function without much disparity. This implies in practice that a linear or ramped injection protocol may be used instead of a strictly exponential injection when the injection duration is not too long and when the decay coefficient is relatively small (for example, the exponential curve with 0.007 decay coefficient in FIG. 3). in addition, a subtle discrepancy in enhancement from a slightly different approximation of exponential function may be indiscernible because of intrinsic physiological fluctuations in enhancement caused by vascular pulsation and respirator motion. However, these are all included as part of the present invention in accordance with the teaching herein.

The data demonstrates that biphasic injections were not sufficient to generate a uniform vascular enhancement. In the study, multiphasic injections were generated with subsecond temporal resolution by the prototype injector. However, this degree of high temporal resolution may not be necessary. The number and interval of temporal steps required in multiphasic injection depends on the injection duration and exponential decay coefficients. Although the effect of temporal resolution on the enhancement produced by multiphasic injections has not been fully explored, multiphasic temporal resolution of 2–3 seconds appears sufficient to generate uniform enhancement because of intrinsic physiological fluctuation. This factor presents another reason why strict adherence to all exponential decay function is not necessary in order to achieve clinically satisfactory and uniform vascular enhancement.

Figure 11:
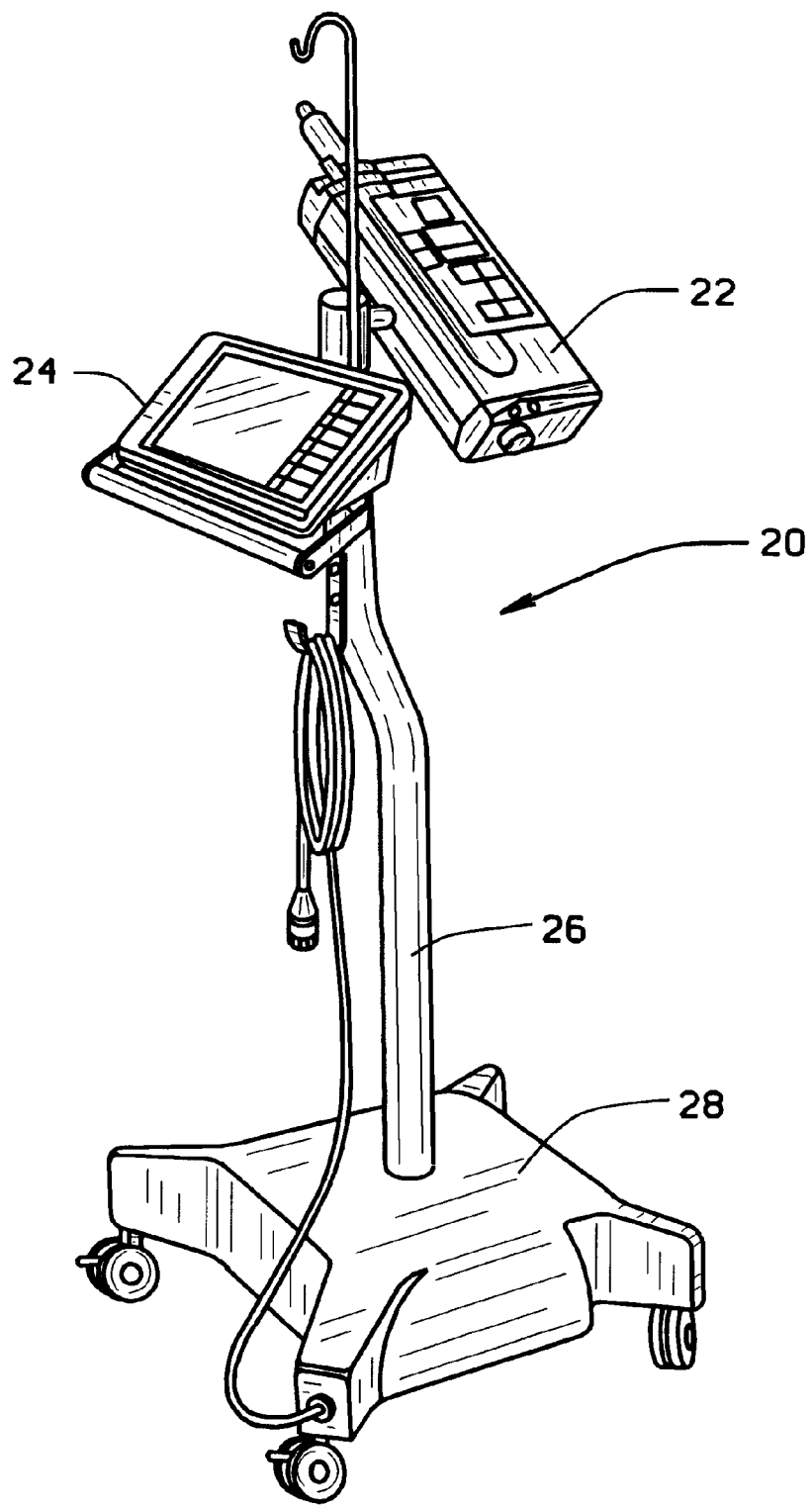
FIG. 11 is a perspective view of a contrast injector programmed to provide multiphasic injections.

The particular contrast injector or delivery system which is thought by the inventors to be particularly useful for implementation of the present invention includes a computer, or other digitally programmable control, for providing operator input and control of the injection protocol. In particular, a Liebel-Flarsheim model CT 9000 ADV Contrast Delivery System, as depicted in FIG. 11, represents such a contrast injector. As shown therein, the contrast delivery system 20 includes a power head 22 for accepting the syringe containing the contrast medium, a control console 24 which may be a LCD display to provide for operator input and control of the injector, and a stand 26 with a base 28 containing the computer or other digital controller.

In the subject injector, the injection parameters are entered in phases. Each phase has a constant flow, a volume and an optional delay. These parameters are displayed on the injector control console 24 and the operator can change the values. Typically, an operator can enter up to four phases. The injector then performs the injection by executing these phases in sequential order. For the injector of the present invention, the parameters of the 2nd phase were changed and the console screen redesigned to allow the operator to enter the parameters for an injection with an exponentially decaying flow rate. The operator enters the exponential coefficient and an elapsed time in order to define the injection protocol. The initial flow rate for the 2nd phase is the flow rate of the 1st phase. This arrangement allows the operator flexibility to experiment with different injection profiles that may include steady state flows before and/or after the exponential decaying flow. In the prototype injector, the 1st flow was used to allow the selected flow rate to reach steady state (approximately 2 mL of volume) and the 3rd phase was not used. The flow chart for, and the particular software program used in, the prototype injector are included as Appendix B. Also included as part of Appendix B are the validation data which includes the data obtained by measuring during an injection the syringe volume versus time using a linear position transducer. A plot of this data is included, and compared with a calculated graph of the exponential curve desired to be obtained. As shown, the actual result curve is a close approximation of the theoretical curve.

While the invention has been disclosed and described in the form of a preferred embodiment, the inventors contemplate that various changes and variations may be envisioned by those of ordinary skill in the art without departing from the invention. For example, the digital control and vagaries of actual devices may well result in injection protocols which are not truly exponential curves. Furthermore, as mentioned above, other factors may serve to limit how close an injection rate may approximate an exponential curve. However, such variations are included within the teaching of the present invention as well as other modifications including changes to the particular injector. For example, virtually any logically controlled injector would be able to perform a multiphasic injection protocol and the invention should not be considered to be limited to a computer controlled, or even a digitally controlled injector. While operator input is usually considered as desirable, a preprogrammed or instructed or wired injector which is set up to perform a multiphasic injection protocol is also considered to be part of the present invention. Indeed, the invention should be considered as being limited only by the scope of the claims appended hereto, and their legal equivalents.

APPENDIX A

To develop governing equations for the model in FIG. 2, mass balance equations are written for each compartment with input and output contrast flow.

$$Vv \frac{dCv}{dt} = Qc(t)Cc - QvCv(t) \qquad [1]$$

$$Vr \frac{dCr}{dt} = QvCv(t) + QsCs(t) - QrCr(t) \qquad [2]$$

$$Vp \frac{dCp}{dt} = QrCr(t) - QpCp(t) \qquad [3]$$

$$Vl \frac{dCl}{dt} = QpCp(t) - QlCl(t) \qquad [4]$$

$$Vs \frac{dCs}{dt} = QlCl(t) - QsCs(t) \qquad [5]$$

subject to the initial conditions at time t=0:

$$Cv(0)=0, \; Cr(0)=0, \; Cp(0)=0, \; Cl(0)=0, \; Cs(0)=0 \qquad [6]$$

where Cv(t), Cr(t), Cp(t), Cl(t), and Cs(t) represent the concentration of the contrast with respect to time, t, within the peripheral venous, right heart, pulmonary, left heart (aorta), and systemic compartments respectively. The Vv, Vr, Vp, Vl, and Vs are: the volumes of the various compartments which are assumed constant. These blood flow and volume of each compartment are determined from known physiologic data. The Qv, Qr, Qp, Ql, and Qs represent the flows. Qc(t) and Cc are the time-dependent flow and concentration of the injected contrast material. The flow in each compartment equals the cardiac output, Q:

$$Q=Qr=Qp=Ql=Qs.$$

Equations 1–6 can be numerically solved to predict and simulate an aortic enhancement curve for a given contrast injection condition. An example in a porcine model with 2 mL/s uniphasic injection is shown in FIG. 4.

Conversely, these differential equations can be used to estimate an input contrast injection algorithm that generates a uniform, prolonged vascular enhancement, i.e. solving an inverse problem, as shown below. Because the initial contrast concentrations in the body compartments equal zero, taking the Laplace Transform of equations [1]–[5] yields $$s(Vs\underline{Cv}(s)) = \underline{Qc}(s)Cc - Qv\underline{Cv}(s) \quad [7]$$

$$s(Vr\underline{Cr}(s)) = Qv\underline{Cv}(s) + Q(\underline{Cs}(s) - \underline{Cr}(s)) \quad [8]$$

$$s(Vp\underline{Cp}(s)) = Q(\underline{Cr}(s) - \underline{Cp}(s)) \quad [9]$$

$$s(Vl\underline{Cl}(s)) = Q(\underline{Cp}(s) - \underline{Cl}(s)) \quad [10]$$

$$s(Vs\underline{Cs}(s)) = Q(\underline{Cl}(s) - \underline{Cs}(s)) \quad [11]$$

where Cv(s), Cr(s), Cp(s), Cl(s), Cs(s), and Qc(s) are the Laplace Transforms of Cv(t), Cr(t), Cp(t), Cl(t), Cs(t), and Qc(t) respectively. A uniform aortic enhancement profile, i.e. constant Cl(t), can be modeled effectively by letting $$\underline{Cl}(s) = a\underline{H}(s) = \frac{\alpha}{s} \quad [12]$$

where a is a scaling constant and H(s) is the Laplace Transform of the Heaviside step-function, H(t):

$$H(t) = \begin{Bmatrix} 0, & t < 0 \\ 1, & t \geq 0 \end{Bmatrix}$$

Combining [12] and [7]–[11], $$Qc(s) = \frac{(sVv + Q)\alpha}{sCcQv}\left\{\frac{(sVr + Q)(sVp + Q)(sVl + Q)}{Q^2} - \frac{Q^2}{(sVs + Q)}\right\} \quad [13]$$

The inverse Laplace Transform of [13] gives the desired result:

$$Qc(t) = \frac{\alpha}{CcQv}\left\{QQv - \frac{Q^2VvE^{\frac{-Qt}{Vs}}}{Vs} - \left(1 - E^{\frac{-Qt}{Vs}}\right)QQv + \right.$$

$$(QvVl + QvVp + QvVr + QVv)\delta(t) +$$

$$\left(\frac{(QvVlVp + QvVlVr + QvVpVr)}{Q} + VlVv + VpVv + VrVv\right)\delta'(t) +$$

$$\left(\frac{QvVlVpVr}{Q} + VlVpVr + VlVrVv + VpVrVv\right)\frac{\delta^{(2)}(t)}{Q} +$$

$$\left.\frac{VlVpVrVv\delta^{(3)}(t)}{Q^2}\right\}. \quad [14]$$

Equation [14] can be approximated by eliminating the terms involving the Dirac delta function, d(t), and its derivatives since these terms contribute only to the impulse rise in contrast concentration immediately following t=0 and not to the steady-state behavior. Without these terms, [14] simplifies to $$Qc(t) \cong \frac{Q\alpha(QvVs - QVv)}{CcQvVs}E^{\frac{-Qt}{Vs}} = \text{(initial injection rate)} * E^{\frac{-Qt}{Vs}}. \quad [15]$$

The parameters forming multiplication terms outside the exponential term in this equation are independent of time and normalized by normalization constant 'α' to set as the initial injection rate.

What is claimed is:

1. A method for substantially maintaining a desired level of vascular enhancement in a patient substantially throughout a desired interval of an injection routine by intravascularly injecting a contrast agent, said method comprising the steps of:
   beginning the injection routine desired interval substantially at a preselected initial injection rate, and
   controllably decreasing the injection rate during the injection routine.

2. The method of claim 1 wherein the decreasing step comprises ramping the injection rate during at least part of the injection routine desired interval.

3. The method of claim 2 wherein the ramping is performed substantially throughout the entirety of the injection routine desired interval.

4. The method of claim 1 wherein the decreasing step comprises decreasing the injection rate at substantially an exponential rate having a decay coefficient approximating a selected cardiac output per body weight typifying the patient.

5. The method of claim 1 further comprising the steps of determining a volume of contrast agent to be used during the injection routine, determining a desired level of enhancement to be attained, and determining the desired interval during which the desired level of enhancement is to be substantially achieved.

6. The method of claim 5 further comprising the step of adjusting the initial injection rate in proportion to the selected cardiac output typifying said patient.

7. The method of claim 1 further comprising the step of adjusting the initial injection rate in proportion to a selected cardiac output per body weight typifying the patient.

8. The method of claim 1 wherein said injection rate is decreased at rate equal to a substantially linear approximation of an exponential function having as its decay coefficient a value directly proportional to a cardiac output per body weight typifying the patient.

9. A method for substantially maintaining a desired level of vascular enhancement in a patient substantially throughout a desired interval of an injection routine by intravascularly injecting a contrast agent, said method comprising the steps of:
   beginning the injection routine desired interval at a preselected initial injection rate, and
   substantially continuously reducing the injection rate as the routine continues.

10. The method of claim 9 wherein the step of continuously reducing the injection rate includes the step of reducing it at substantially an exponential rate having a decay coefficient approximating a selected cardiac output per body weight typifying the patient.

11. The method of claim 10 further comprising the steps of determining a volume of contrast agent to be used during the injection routine, determining a desired level of enhancement to be attained, and determining the desired interval during which the desired level of enhancement is to be substantially achieved.

12. The method of claim 11 further comprising the step of adjusting the initial injection rate in proportion to said selected cardiac output.

13. The method of claim 9 wherein said injection rate is reduced at a rate equal to a substantially linear approximation of an exponential function having as its decay coefficient a value directly proportional to a cardiac output per body weight typifying the patient.

14. A method for substantially maintaining a desired level of vascular enhancement in a patient substantially throughout a desired interval of an injection routine by intravascularly injecting a contrast agent, said method comprising the steps of:

beginning the injection routine substantially at a preselected initial injection rate, and substantially continuously reducing the injection rate at a reduction rate calculated to be substantially dependent on a selected cardiac output per body weight typifying the patient.

15. The method of claim 14 wherein said reduction rate is an exponential function having as its decay coefficient a value directly proportional to cardiac output per body weight typifying the patient.

16. The method of claim 14 wherein said reduction rate is a substantially linear approximation of an exponential function having as its decay coefficient a value directly proportional to a cardiac output per body weight typifying the patient.

17. A method for substantially maintaining a desired level of vascular enhancement in a patient substantially throughout a desired interval of an injection routine by intravascularly injecting a contrast agent, said method comprising the steps of:

implementing a multiphasic injection protocol for injection of said contrast agent.

18. The method of claim 17 further comprising the step of beginning the injection routine substantially at a preselected initial rate.

19. The method of claim 18 wherein said multiphasic injection protocol is an exponential function.

20. The method of claim 19 wherein said exponential function has a decay coefficient of approximately 0.01.

* * * * *